June 21, 1938. L. A. MICHLER Plant Pat. 281
SNAPDRAGON
Filed May 15, 1937
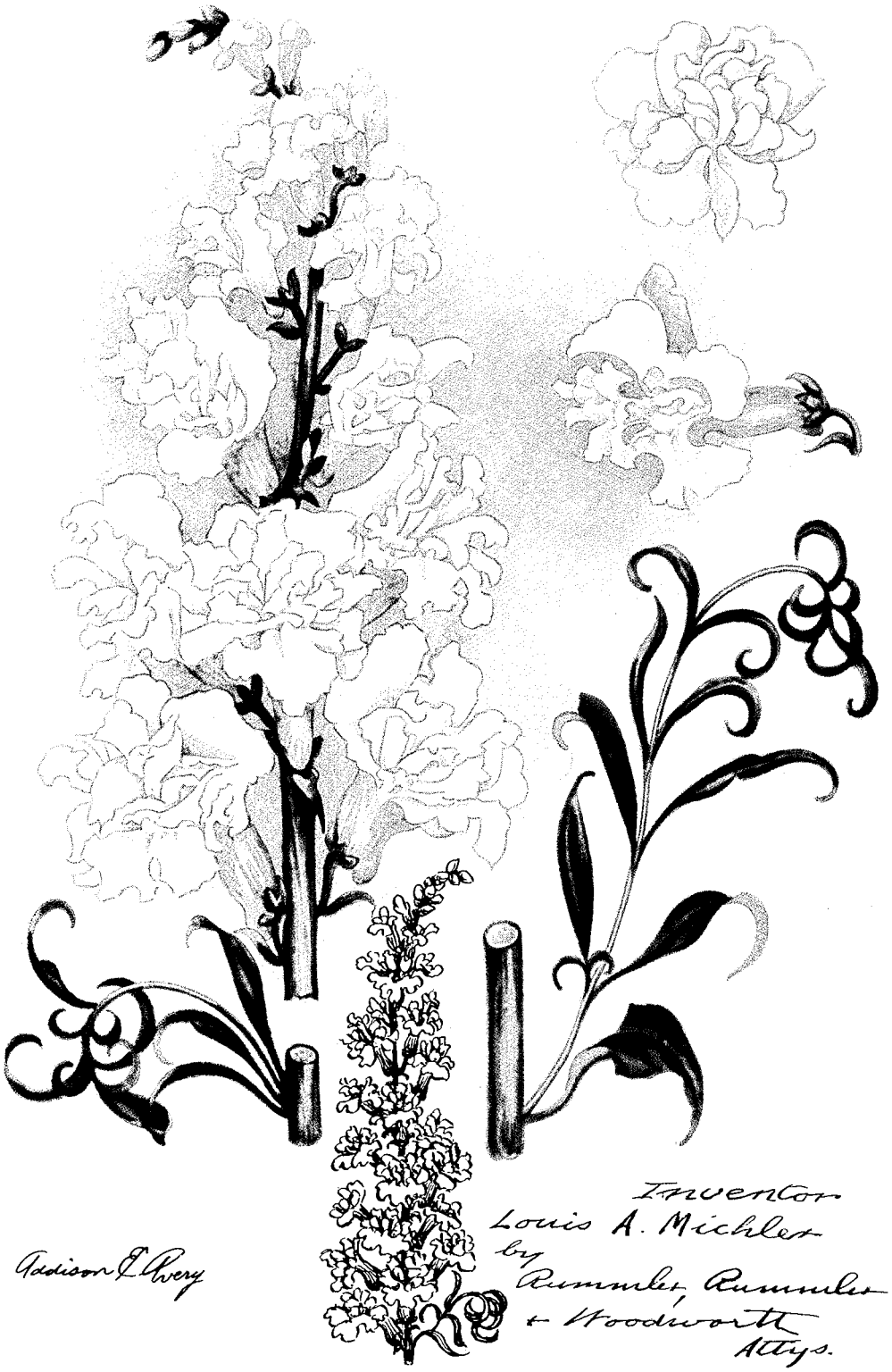
Inventor
Louis A. Michler
by
Rummler, Rummler
& Woodworth
Attys.
Addison J. Avery Patented June 21, 1938

Plant Pat. 281

UNITED STATES PATENT OFFICE

281

SNAPDRAGON

Louis A. Michler, Lexington, Ky., assignor to Michler Florist, Inc., a corporation of Kentucky Application May 15, 1937, Serial No. 142,740

1 Claim. (Cl. 47—60)

The new variety of Antirrhinum herein illustrated and described was developed from seeds which I purchased from a Michigan firm under the trade-name "Daybreak", and originated with a single odd seedling in a large number of otherwise uniformly normal seedling plants from which the subject plant distinguished decisively in physical characteristics, color and fragrance. This odd seedling was saved and propagated and the new shoots which were developed reproduced the original.

In the new plant the blossoms are less massed on the blossom spikes than in more common kinds of snapdragons. There is an abnormal superdoubleness of each blossom with color like that of the Briarcliff rose. The fragrance is similar to that of trailing arbutus and the length of the bloom cluster or spike is about 15 inches. There are about 28 individual blossoms to a spike. Normally the main stalks of the plant grow from three to five feet tall, the height depending upon the number of shoots on a stool which is generally from three to five. If the growth is substantially limited to one stalk, that will be about six feet long.

It has been impossible to obtain seeds from the plant but cuttings therefrom promptly take root in soil with ease and in a single growing season it is possible to produce 1,000 new plants by such process with only one plant to start with.

The accompanying drawing shows in color the upper end of a bloom spike and detached therefrom, the lower end of the stalk, to illustrate the lanceolate form of the leaves. In black and white is a sketch of an entire bloom spike. To the right of that is a section of a stalk having a lateral shoot such as is sub-divided for the production of new plants. Above this view are side and face views of a single bloom.

The plant is a greenhouse production and has not been tried out of doors. The flower spikes when cut from the plant and placed in water will continue to open as customary with snapdragons, but will last from two to four weeks indoors, and do not shed petals.

Noticeable physical characteristics of the plant are the rather large and thick stalks with white pith, and fairly uniform spacing of the blooms on the spikes, and the more closely spaced or clustering of the buds at the top of the spike, and the thin lanceolate form of the leaves. The individual flowers average somewhat more than two inches in length and have a bilabiate, large-throated corolla tube about one-third the length of the flower. As with other snapdragons, the corolla is saccate in form and swells by a regular curve into oppositely disposed, notched ears formed at its upper end. These ears terminate in lobes, the upper one consisting of two lobes and the lower of three lobes with revolute margins. Where yellow eyes or peaks show, the flower is slightly pubescent. The flowers are in acropetal succession and grow singly between the angle of a bract and the peduncle. There is invariably a graceful spacing of the flowers.

The color of the bloom is pinkish with touches of yellow and white, as illustrated. As scheduled below, these colors correspond approximately with those shown by Maerz & Paul's Dictionary of Color as follows:

| Section | Color | Plate | Letter | No. |
|---|---|---|---|---|
| Main outside petals | | 1 | A | 3 |
| Outer edge deeper shade | | 1 | A | 5 |
| Tipped with | Cadmium Lemon. | 9 | L | 1 |
| | and Dandelion | 9 | L | 4 |
| Inside cluster small petals | | 1 | A | 3 |
| Corolla-tube | Ashes of Rose | 4 | A | 4 |
| Blending into | Bistre Green | 13 | L | 5 |
| Some blossoms near tip of stalk have marked projection of white petals. | | 1 | A | 1 |
| With | Cadmium Lemon at base. | 9 | L | 1 |
| Small blossoms at tip of stalk | | | | |
| Outer petals | | 1 | B | 1 |
| With centers | | 1 | A | 1 |
| Shading off to blossoms at very tip of stalk. | Milk White | 9 | B | 1 |
| Buds | | 18 | I | 2 |
| Extreme tip buds | Lettuce Green | 20 | L | 5 |
| Main stalk and leaf stem | | 20 | L | 7 |
| Leaves (curly) | Brunswick Green. | 22 | L | 10 |
| Center of stalk | | 18 | A | 1 |

I claim:

The herein disclosed variety of snapdragon (Antirrhinum) having stalks from three to five feet in length, superdouble bloom, bloom spikes generally having a length of about fifteen inches with individual blossoms distinctly spaced, color similar to the Briarcliff rose, fragrance like trailing arbutus, strong ability of cuttings of the plant to take root, and peculiar staying quality of the cut flower.

LOUIS A. MICHLER.